US010544067B2

(12) United States Patent
Minoux et al.

(10) Patent No.: US 10,544,067 B2
(45) Date of Patent: Jan. 28, 2020

(54) PROCESS FOR PREPARING OLEFINS BY DEHYDRATING ALCOHOLS WITH LESS SIDE EFFECTS COMPRISING ADDITION OF ORGANIC ACIDS

(71) Applicants: Total Research & Technology Feluy, Seneffe (Feluy) (BE); IFP Energies Nouvelles, Rueil Malmaison (FR)

(72) Inventors: Delphine Minoux, Nivelles (BE); Nikolai Nesterenko, Nivelles (BE); Cindy Adam, Wierde (BE); Walter Vermeiren, Houthalen (BE); Philip De Smedt, Sint-Niklaas (BE); Jean-Pierre Dath, Beloeil (BE); Vincent Coupard, Villeurbanne (FR); Sylvie Maury, Saint Maurice d'Argoire (FR); Nicolas Aribert, Moirans (FR)

(73) Assignee: TOTAL RESEARCH & TECHNOLOGY FELUY, Seneffe (BE)

( * ) Notice: Subject to any disclaimer, the term of this patent is extended or adjusted under 35 U.S.C. 154(b) by 187 days.

(21) Appl. No.: 15/540,318

(22) PCT Filed: Dec. 18, 2015

(86) PCT No.: PCT/EP2015/080436
§ 371 (c)(1),
(2) Date: Jun. 28, 2017

(87) PCT Pub. No.: WO2016/107758
PCT Pub. Date: Jul. 7, 2016

(65) Prior Publication Data
US 2019/0092706 A1    Mar. 28, 2019

(30) Foreign Application Priority Data
Dec. 31, 2014  (EP) .................................... 14290403

(51) Int. Cl.
C07C 1/24 (2006.01)
B01J 29/40 (2006.01)
B01J 21/04 (2006.01)
B01J 21/12 (2006.01)
B01J 29/65 (2006.01)
B01J 29/86 (2006.01)
C07C 11/04 (2006.01)

(52) U.S. Cl.
CPC ................ C07C 1/24 (2013.01); B01J 21/04 (2013.01); B01J 21/12 (2013.01); B01J 29/40 (2013.01); B01J 29/65 (2013.01); B01J 29/86 (2013.01); C07C 11/04 (2013.01); C07C 2521/04 (2013.01); C07C 2521/12 (2013.01); C07C 2529/65 (2013.01); C07C 2529/85 (2013.01)

(58) Field of Classification Search
CPC ....... C07C 1/24; C07C 11/04; C07C 2527/14; C07C 2529/06; C07C 2529/40; B01J 29/40; B01J 29/85; B01J 37/10; B01J 37/28
See application file for complete search history.

(56) References Cited

U.S. PATENT DOCUMENTS

| | | | |
|---|---|---|---|
| 3,911,041 A | 10/1975 | Kaeding et al. | |
| 4,232,179 A | 11/1980 | Valladares et al. | |
| 4,396,789 A | 8/1983 | Barrocas et al. | |
| 4,423,270 A | 12/1983 | Pearson | |

(Continued)

FOREIGN PATENT DOCUMENTS

| | | |
|---|---|---|
| EP | 2 108 636 A1 | 10/2009 |
| WO | 2009016153 A1 | 2/2009 |

(Continued)

OTHER PUBLICATIONS

Nieskens et al.; "Effect of Oxygenate Impurities on the Conversion of Alcohols to Olefins"; Industrial & Engineering Chemistry Research 2014, 53, 10892-10898.

(Continued)

Primary Examiner — Sharon Pregler
(74) Attorney, Agent, or Firm — Albert Shung

(57) ABSTRACT

The present invention is a process for dehydrating an alcohol to prepare corresponding olefin(s), comprising:
(a) providing a feed (A) comprising at least an alcohol having at least 2 carbon atoms, and preferably at most 5 carbon atoms, or a mixture thereof optionally water, optionally an inert component, in a dehydration unit,
(b) placing the feed (A) into contact with an acidic catalyst in a reaction zone of said dehydration unit at conditions effective to dehydrate at least a portion of the alcohol to make an olefin or a mixture of olefins having the same number of carbon atoms as the alcohol,
(c) recovering from said dehydration unit an effluent (B) comprising:
an olefin or a mixture of olefins,
water,
undesired by-products including aldehydes and lighter products resulting from degradation of said aldehydes under the conditions of step (b),
optionally unconverted alcohol(s) if any,
optionally the inert component,
wherein,
said feed (A)-providing step (a) comprises adding an effective amount of one or more organic compound capable to reduce the undesired by-products by comparison with a non introduction of such compound, said organic compound being chosen among organic acids.

13 Claims, No Drawings

(56) References Cited

U.S. PATENT DOCUMENTS

| | | | |
|---|---|---|---|
| 4,602,119 A * | 7/1986 | Drake | C07C 1/24 |
| | | | 502/355 |
| 4,847,223 A | 7/1989 | Le Van Mao et al. | |
| 5,573,990 A | 11/1996 | Wang et al. | |
| 6,797,851 B2 | 9/2004 | Martens et al. | |
| 2008/0261230 A1 | 10/2008 | Liao et al. | |
| 2010/0197485 A1 | 8/2010 | Johnston et al. | |

FOREIGN PATENT DOCUMENTS

| | | |
|---|---|---|
| WO | 2009092779 A2 | 7/2009 |
| WO | 2009092781 A2 | 7/2009 |
| WO | 2011002699 A2 | 1/2011 |
| WO | 2009098262 A1 | 7/2011 |
| WO | 2011089262 A1 | 7/2011 |
| WO | 2011161045 A1 | 12/2011 |
| WO | 2013017496 A1 | 2/2013 |
| WO | 2013017497 A1 | 2/2013 |
| WO | 2013017498 A1 | 2/2013 |

OTHER PUBLICATIONS

International Search Report issued in PCT/EP2015/080436, dated Feb. 17, 2016, 3 pages.

* cited by examiner

PROCESS FOR PREPARING OLEFINS BY DEHYDRATING ALCOHOLS WITH LESS SIDE EFFECTS COMPRISING ADDITION OF ORGANIC ACIDS

CROSS-REFERENCE TO RELATED APPLICATIONS

This application claims the benefit of PCT/EP2015/080436 filed Dec. 18, 2015, which claims priority from EP 14290403.6 filed Dec. 31, 2014, which are incorporated herein by reference in their entireties for all purposes.

FIELD OF THE INVENTION

The present invention relates to dehydration of alcohols to make olefins, in particular to prepare the corresponding olefin, with reduced side reactions, in other words with reduced amount of by-products. "Corresponding olefins" means an olefin having the same number of carbon atoms as the alcohol precursor.

The present invention relates to a method for the dehydration of substantially one single alcohol or a mixture of alcohols characterised by an increased yield for the corresponding olefin with the same number of carbon atoms by lowering the formation of undesired by-products, in particular aldehyde(s) and light products ($H_2$, CO, $CH_4$ ... ), using appropriate spiking of the alcohol feed with a compound chosen among organic acids.

The invention can be used for a dehydration unit comprising any type of reactors (batch, moving, fixed or fluidized bed), the reactors operating either under adiabatic or isothermal conditions. The invention is particularly useful for dehydration units comprising fixed, moving or fluidized bed reactors.

BACKGROUND OF THE INVENTION

Alcohol dehydration reactions to produce alkenes have been known for a long time. Usually these reactions are performed in presence of solid acid catalysts, the conversion of alcohol being nearly complete. However, in view of the potential downstream applications of olefins, it is of particular importance to limit the amounts of secondary products to gain in process efficiency and to save expensive downstream steps of separation/purification.

It has been observed, in addition to dehydration of alcohol to the corresponding olefin, formation of aldehyde, in particular formation of the corresponding aldehyde, and formation of light products such as $H_2$, CO, $CH_4$. It is supposed that formation of $H_2$ and CO results mainly from degradation of said aldehydes under the conditions of the dehydration reactions. Formation of $H_2$ and $CH_4$ may result from other kind of side reactions. For example, during dehydration of ethanol, formation of acetaldehyde, $H_2$, CO, and $CH_4$ is observed. Similar undesirable secondary by-products can be observed during dehydration of other alcohols. These secondary products lead to lower once-through yield of the corresponding olefin and to important losses of the olefin, in particular in downstream purification section. The formation of these products is still not well understood and solutions provided by prior art to reduce the formation of these secondary products are limited.

WO2011/002699 discloses a process for producing olefins by dehydration of alcohols in reactors under either adiabatic or isothermal conditions. The process comprises reacting under first reaction conditions an aliphatic alcohol, optionally diluted with water, in the presence of a dehydration catalyst to form a first reaction product that includes dialkyl ether and generated water, and further reacting under second reaction conditions the first reaction product in the presence of a dehydration catalyst to form olefin by dehydration of the dialkyl ether. The temperature of the second reaction conditions is at least 10° C. higher than the temperature of the first reaction conditions. In particular, the temperature of the first reaction conditions ranges from 200° C. to 450° C., while the temperature of the second reaction conditions ranges from 250° C. to 500° C., preferably from 400° C. to 450° C. The purpose of the relatively low temperature range in the first reactor is to instigate reaction of the aliphatic alcohol to primarily its corresponding dialkyl ether, which dehydration serves to increase the water content of the first reaction product. The effect of the temperature increase between the first and second reactors is that the amount of dialkyl ether may be progressively reduced as dehydration is carried to or toward completion, to form the final desired olefin, and the reduction in starting diluent water with the alcohol feed means that there is a minimum of corresponding aldehyde formed. There is no mention of other by-products such as $H_2$, CO or $CH_4$.

U.S. Pat. No. 4,232,179 relates to a process for preparing ethene by dehydrating ethyl alcohol in the presence of catalysts using adiabatic reactors at high temperature. In that process, the necessary heat to maintain the temperature of the catalyst bed at levels compatible with the desired conversion is supplied by the simultaneous introduction of the feed and a sensible heat carrying fluid, which may be selected from, for example, a part of the effluent from the reactor used as a recycle stream, steam supplied by an external source, other adequate fluids for the process, or any combination thereof. The use of diluted ethyl alcohol in the sensible heat carrying fluid stream leads to considerable reduction in the formation of C3 and C4 by-products, as well as in the deposition of coke over the catalyst, these peculiar features leading to highly pure ethene. There is no mention of other by-products such as $H_2$, CO or $CH_4$.

U.S. Pat. No. 4,396,789 relates to a process for the dehydration of ethanol to form ethene in fixed adiabatic reactors containing a dehydration catalyst. The process includes the recycling of unreacted ethanol to the process, feeding the charge to the initial reactor at a pressure of 20 to 40 atm, withdrawing the ethane from the final reactor at a pressure of no less than 18 atm, and passing at least a portion of said reaction effluent to cryogenic purification with further compression. Ethyl alcohol is introduced with steam at a temperature from 400° C. to 520° C. and a pressure from 20 to 40 atm. Subsequent washing and purification steps permit to obtain a high purity ethene. There is no mention of by-products such as $H_2$, CO or $CH_4$.

WO2011/161045 relates to the dehydration of alcohols on acidic catalysts to make the corresponding olefins. The unselective reactions that need to be suppressed are (i) altering in number of carbon atoms compared to the alcohol through oligomerisation and cracking reactions and (ii) the formation of paraffins and aromatics or coke through hydrogen-transfer reactions. In that process, the activity and selectivity of alcohol dehydration catalyst is adjusted by poisoining the unselective acid sites of the catalyst by spiking the feed with a neutralizing agent while keeping active the selective acidic sites of the catalyst. The neutralizing agent can be chosen from basic compounds: ammonia, organic ammonium salts, hydrazine, nitriles, amines, (including pyridines, pyrrols, pyrrolydones and pyrrolidines), amides, imines, di-imines, imides, cyanates, isocyanates, nitrites and nitroso compounds, aldehydes, ketones, carboxylic esters, and their thio-compounds (thiols, sulphides, disulfides). Secondary light products as $H_2$, CO, $CH_4$ are not mentioned. The spiking is used to moderate the excess of catalyst acidity.

U.S. Pat. No. 4,847,223 discloses the deposition of trifluoromethanesulfonic acid (TFA) onto an acid-form pentasil zeolite to convert ethanol into ethylene. Such acid is coated on the catalyst, HZSM-5 being exemplified. The TFA stays on the catalyst and is not part of the stream of ethanol to be dehydrated.

U.S. Pat. No. 4,423,270 discloses the use of a substituted phosphoric acid as catalyst for dehydration of an ethanol into ethylene. The acid is absorbed on a porous granular support. The acid is therefore not part of the stream of ethanol to be dehydrated.

Nieskens et al. in Industrial & Engineering Chemistry Research 2014, 53, 10892-10898 discloses the addition of a methyl acetate compound at the inlet of the methanol to olefin (MTO) and dehydration reactor. The working conditions to perform those two reactions simultaneously differs from performing the dehydration only as some heat produced by the MTO reactions can readily be used for the dehydration reaction.

E 2 108 636 discloses the used of CO2 as inert component able to bring heat to the dehydration reaction. This document is not concerned about the selectivity of the dehydration reaction.

WO 2013/017496 discloses the dehydration of ethanol over a P-ZSM-5 catalyst. This application discloses a particular catalyst composition tested for the dehydration of the ethanol. However this application is not concerned about the amount of H2, CO, CH4 produced by the catalyst and the way to limit the formation of such by-products.

Prior arts teach us how to improve selectivity in the dehydration products by poisoning the unselective acid sites on the catalyst and inhibit cracking and oligomerization of the alkenes. However, formation of $H_2$, CO, $CH_4$ by-products typically occurs via a different route relative to the acid catalyzed reaction pathway. So, an object of the present invention is to reduce formation of secondary by-products, in particular formation of aldehydes and of light products such as $H_2$, CO, $CH_4$. In particular, the by-products H2, CO, CH4 lead to purification problems downstream the dehydration units as cryogenic temperature are needed in order the separate them from the other components. There is therefore a need for limiting the production of such by-products as much as possible.

A convenient solution has been discovered to reduce the amount of secondary products, light products ($H_2$, CO, $CH_4$) and aldehydes, and to improve the yield of olefin in alcohol dehydration reactions by adding with the alcohol feed organic acid(s).

Without willing to be bound by any theory, it is supposed that metallic sites, which are able to promote the formation of the aldehyde, in particular the corresponding aldehyde, may catalyze side reactions leading to the formation of these secondary by-products. In particular, it is believed that a transformation of the alcohol into the corresponding aldehyde first occurs and is followed by formation of light products such as $H_2$, CO, by degradation of this corresponding aldehyde into lighter products, for example by decarbonylation of the aldehyde. Formation of $CH_4$, but also of some $H_2$, may result from other side reactions, probably catalyzed by the same sites.

The origin of these metallic sites is still uncertain and may be various. They are thought to be present on metallic internal surface of the dehydration unit, in particular metallic internal surface in contact with the feed before the entry of the feed in the reaction zone or in the reaction zone. It is also thought that the sites may also be present on catalyst, either as part of the catalyst or coming from degradation by corrosion of these metallic internal surfaces in contact with the feed. It is also believed that regeneration of the catalyst may lead to an activation of the sites responsible for the formation of the above mentioned undesirable by-products.

Without willing to be bound by any theory, it is supposed that organic acid(s) poison, probably via a stronger adsorption relative to the alcohols, the sites on which these secondary products are formed. It seems that organic compound with an acidic character can selectively poisons the most active sites, which dramatically reduces side reactions and improves the yield of olefin.

BRIEF SUMMARY OF THE INVENTION

An object of the present invention is a process for dehydrating an alcohol to prepare corresponding olefin(s), comprising:

(a) providing a feed (A) comprising at least an alcohol having at least 2 carbon atoms, and preferably at most 5 carbon atoms, or a mixture thereof, optionally water, optionally an inert component, in a dehydration unit, (b) placing the feed (A) into contact with an acidic catalyst in a reaction zone of said dehydration unit at conditions effective to dehydrate at least a portion of the alcohol to make an olefin or a mixture of olefins having the same number of carbon atoms as the alcohol, (c) recovering from said dehydration unit an effluent (B) comprising:
an olefin or a mixture of olefins,
water,
undesired by-products including aldehydes, in particular the corresponding aldehydes, and light products, comprising $H_2$, CO, $CH_4$,
optionally unconverted alcohol(s) if any,
optionally the inert component,
wherein,
said feed (A)-providing step (a) being further remarkable in that an effective amount of one or more compounds capable to reduce the undesired by-products by comparison with a non introduction of such compound is added to said feed (A) at step (a) at a weight concentration of at least 0.05 wt % preferably at least 0.1 wt % more preferably at least 0.5 wt % and at most 5 wt % preferably at most 2 wt % and more preferably at most 1 wt % of the total content of said feed (A) with said compound, said compound being chosen among organic acids. It is also further remarkable in that said acidic catalyst is at least one compound selected from the group consisting of:
A crystalline silicate zeolite having a ratio Si/Al higher than 10,
A dealuminated crystalline silicate zeolite,
A phosphorous modified zeolite,
silica-alumina,
alumina,
silicated, titanated, zirconated or fluorinated alumina
silico-aluminophosphates,
a modified crystalline aluminosilicate of the Framework Type FER having Si/Al framework molar ratio greater than 20 and a ratio between strong acid sites and weak acid sites, S/W, lower than 1.0, the ratio S/W being measured by temperature-programmed desorption of ammonia and being determined by the ratio of the peak area of ammonia desorbed above 340° C. to that desorbed below 340° C., or any of above cited acidic catalyst, which was subjected to a preliminary pre-coking step.

As a result of said addition of compound with an acidic character, the formation of undesired by-products is reduced and yield for the desired corresponding olefin is increased.

The present invention is particularly useful for dehydrating units presenting at least one metallic internal wall, in particular containing iron such as steel. Said metallic internal wall may be part of a reactor, pipe or any other equipment of the dehydrating unit in contact with feed (A).

With regards to said effluent (B) of the dehydration unit, the corresponding aldehyde means aldehydes resulting from the transformation of an alcohol contained in the feed (A) with the same number of carbon atoms. The light products are mainly $H_2$, CO, $CH_4$. Some light products result from degradation of said aldehydes are alkenes of lower number of carbon atoms than the aldehyde, or gaseous compounds such as $H_2$, CO.

In another specific embodiment, said effective amount of one or more compound capable to reduce the undesired by-products by comparison with a non introduction of such compound is determined with the following steps:

performing said dehydration of step (b) without introducing said organic compound chosen among organic acids in stream (A)

measuring said content of undesired by-products including aldehydes and light products, comprising $H_2$, CO, $CH_4$, in said effluent (B) obtained at step (b)

increasing the content of said compound being chosen among organic acids to feed (A) prior to step (b) in the total content of said feed (A) by increments of 0.05 wt % until the total content of undesired by-products including aldehydes and light products, comprising $H_2$, CO, $CH_4$, in said effluent (B) obtained at step (b) is lower than 4 wt %.

In another specific embodiment, said process for dehydrating an alcohol to prepare corresponding olefin(s) comprises the step of recycling said unconverted alcohol if any with said undesired by-products being, preferably organic acids, at the inlet of the dehydration. It has been particularly discovered that the undesired by-products include organic acids. Such undesired by-products being organic acids can be recycled at the inlet of the dehydration unit. By doing it is possible to reduce the amount of organic acids capable to reduce the undesired by-products by comparison with a non introduction of such organic acid added to said feed (A) at step (a) while still maintaining the production of un-desired by-products at the exit of said dehydration unit at the level obtained without said recycling. In other word, the addition of fresh organic acids (i.e. organic acids that does not exit from the dehydration unit) before being introduced feed (A) at step (a) is limited so that the overall of organic acids (fresh and recycled) content in said feed (A) entering the dehydration unit is at the same level as if there was not recycling. It has also been discovered that a relative equilibrium for the production of un-desired by product including organic acids is quickly reached when said unconverted alcohol is recycled. During the start up of the unit, a large quantity of "fresh" organic acids should be added at the inlet of the dehydration unit, then the equilibrium is reached and the "fresh" organic acids introduced shall be reduced as some organic acids are recycled.

In a specific embodiment, said feed (A)-providing step comprises adding one or more compound(s) chosen among organic acid to the feed (A) or directly in the dehydration unit or contained in a stream recovered from step (c) and recycled back to step (a). Said stream recovered from step (c) and recycled back is for example non converted alcohol, water or inert diluents.

According to a specific embodiment:
the recovery step (c) comprises recovering unconverted alcohol(s),
said process further comprising, subsequent to recovery step (c), a step of:
(d) recycling the unconverted alcohol to said feed (A)-providing step (a), in the dehydration unit.

According to a specific embodiment, the recovering step (c) may comprise recovering the olefin(s) and the unconverted alcohol(s), as well as each compound contained in the effluent (B), by means of fractionating.

In an embodiment the acidic catalyst is at least one compound selected from the group consisting of:
A crystalline silicate zeolite having a ratio Si/Al higher than 10,
A dealuminated crystalline silicate zeolite,
A phosphorous modified zeolite,
silica-alumina,
alumina,
silicated, titanated, zirconated or fluorinated alumina
silico-aluminophosphates,
a modified crystalline aluminosilicate of the Framework Type FER having Si/Al framework molar ratio greater than 20 and a ratio between strong acid sites and weak acid sites, S/W, lower than 1.0, the ratio S/W being measured by temperature-programmed desorption of ammonia and being determined by the ratio of the peak area of ammonia desorbed above 340° C. to that desorbed below 340° C., or any of above cited acidic catalyst, which was subjected to a preliminary pre-coking step.

In a specific embodiment, said olefin(s) recovered in step c) may be used for production of polymers and elastomers, in particular after appropriated purification and transformation. In another specific embodiment, said olefin(s) recovered in step c) may be used form production of fuel, in particular after appropriated purification and transformation.

DETAILED DESCRIPTION OF THE INVENTION

As regards the feed provided at step (a), the alcohol is any alcohol provided it can be dehydrated to the corresponding olefin, having a same number of carbon atoms. By way of example mention may be made of alcohols having from at least 2 to 5 carbon atoms, preferably from at least 2 to 4 carbon atoms. Advantageously, the invention is of particular interest for ethanol, propanol, butanol (iso, n and tertio).

The feed provided at step (a) can be a mixture of the above alcohols in any proportions, in particular a mixture of ethanol and propanol. The alcohols contained in the mixture may have the same number of carbon atoms or different number of carbon atoms.

Preferably, the alcohol may be ethanol, propanol, isopropanol, 1-butanol, 2-butanol, isobutanol, pentan-1-ol, 3-Methylbutan-1-ol, 2-Methylbutan-1-ol, 2,2-Dimethylpropan-1-ol, pentan-3-ol, Pentan-2-ol, 3-Methylbutan-2-ol, 2-Methylbutan-2-ol, or mixture thereof.

Preferably, the alcohol(s) is (are) provided from biomass fermentation or biomass gasification to syngas followed by a modified Fischer-Tropsch synthesis. As such, the alcohol(s) may contain impurities such as organic acids in a content of less than 100 wppm related to the alcohol(s).

For example, the alcohol(s) may be bio-alcohol(s) issued from edible or non-edible biomass. Such bio-alcohols may be obtained by any existing route, for example via hydrogenation of corresponding aldehydes, ketones or acids issued from edible or non-edible biomass.

The alcohol(s) may also be obtained via syn-gas route or synthesized via partial oxidation of paraffin.

Alcohols, in particular ethanol, thus far are the only renewable liquid fuel produced in commercial quantities primarily by the fermentation of sugars for use as a blending component in gasoline.

Most of the world's ethanol is produced by fermentation, using edible biomass such as crops in particular sugar cane, sugar beet, corn, rice and maize. Municipal waste (non edible biomass) can also be used as feedstock, reducing landfill disposal and turning rubbish into a valuable product. For instance, such a process might proceed by the conversion of sucrose by the enzyme invertase into glucose and fructose, then the conversion of glucose by the enzyme zymase into ethanol (and carbon dioxide).

Recently, new biochemical routes have been developed to produce selectively isobutanol from carbohydrates. The new strategy uses the highly active amino acid biosynthetic pathway of microorganisms and diverts its 2-keto acid intermediates for alcohol synthesis. 2-Keto acids are intermediates in amino acid biosynthesis pathways. These metabolites can be converted to aldehydes by 2-keto-acid decarboxylases (KDCs) and then to alcohols by alcohol dehydrogenases (ADHs). Two non-native steps are required to produce alcohols by shunting intermediates from amino acid biosynthesis pathways to alcohol production (US patent 2008/0261230). Recombinant microorganisms may be required to enhance the flux of carbon towards the synthesis of 2-keto-acids. For example, in the valine biosynthesis 2-ketoisovalerate is an intermediate. Glycolyse of carbohydrates results in pyruvate that is converted into acetolactate by acetolactate synthase. 2,4-dihydroxyisovalerate is formed out of acetolactate, catalysed by isomeroreductase. A dehydratase converts the 2,4-dihydroxyisovalerate into 2-ketoisovalerate. In the next step, a keto acid decarboxylase makes isobutyraldehyde from 2-keto-isovalerate. The last step is the hydrogenation of isobutyraldehyde by a dehydrogenase into isobutanol.

Non-edible biomass, like cellulosic materials are both sustainable and available in large quantities.

Strategy of the alcohols production from non-edible biomass, including cellulosic biomass such as wood chips, corn stover, corn cobs and municipal solid waste, is based either on biochemical approaches or on a thermochemical approach.

Three core biochemical conversion technologies enable the conversion of biomass into ethanol: (a) pretreatment (including prehydrolysis), (b) saccharification or hydrolysis and (c) fermentation. Pretreatment involves milling and exposure to chemicals and heat to reduce the size of the plant fibers and hydrolyze a portion of the material to yield fermentable C5 sugars. Saccharification utilizes enzymes to hydrolyze another portion to C6 sugar. Bioengineered microorganisms ferment the various sugars to chemical products in fermentation.

Recent advances in biotechnology have led to the development of the microorganisms to produce ethanol via fermentation from the five sugars in cellulose (arabinose, galactose, glucose, mannose and xylose).

The thermochemical approach considers gasification of biomass or bio-methane to syngas followed by chemical synthesis of ethanol or heavy alcohols over heterogeneous catalyst from syngas.

The syngas could be also converted via microbial fermentation to ethanol. The technology is commercial and is offering by several companies. Coskata claims to have proprietary microorganisms that can convert syngas into useful chemicals or fuels, and LanzaTech has been operating a pilot plant in New Zealand.

Another option is to converts syngas, to methanol which is reacted with CO to produce acetic acid. The acetic acid could be further converted to ethanol by hydrogenation. The hydrogenation step would be conducted in the vapor phase using, for example a Pt—Sn catalyst (US 2010/0197485).

The inert component optionally provided in step (a) is any component provided there is no adverse effect on the catalyst. Because the dehydration is endothermic the inert component can be used to bring energy. By way of examples the inert component is selected among the saturated hydrocarbons having up to 10 carbon atoms, naphtenes, nitrogen. An example of inert component can be any individual saturated compound, a synthetic mixture of the individual saturated compounds as well as some equilibrated refinery streams like straight naphtha, butanes etc. Advantageously it is a saturated hydrocarbon or a mixture of saturated hydrocarbons having from 3 to 7 carbon atoms, more advantageously having from 4 to 6 carbon atoms and is preferably pentane.

The weight proportions of respectively alcohols, water and inert component are, for example, 5-100/0-95/0-95 (the total being 100). The feed (A) can be liquid or gaseous. Depending on the type of the reaction zone (in batch or continuously), the feed (A) may be provided as a flowing stream.

As regards the reaction zone of the dehydration unit, it can comprise one or several reactors in series or in parallel. Reactor(s) may be a batch reactor, fixed bed reactor (radial, isothermal, adiabatic etc), a moving bed reactor or a fluidized bed reactor. A typical fluid bed reactor is one of the FCC type used for fluidized-bed catalytic cracking in the oil refinery. A typical moving bed reactor is of the continuous catalytic reforming type.

The dehydration reactions may be performed continuously in a fixed bed reactor configuration using several reactors in series of equal or different sizes or a pair of parallel "swing" reactors. The various preferred catalysts of the present invention have been found to exhibit high stability. This enables the dehydration process to be performed continuously in two parallel "swing" reactors wherein when one reactor is operating, the other reactor is undergoing catalyst regeneration. The catalyst used in the present invention also can be regenerated several times.

The invention is particularly adapted to moving or fluidized bed reactors. In such reactors, the moving particles of catalyst have an abrasive effect on the reactor wall avoiding the deposition of any coating. The internal surface of the reactor thus remains clean, which may favour the formation of secondary reactions. Addition of the organic compound(s) with acidic character during the process permits to reduce these secondary reactions.

The dehydration unit may further comprise one or more other zones such as a heating zone for heating the feed before its entry into in the reaction zone, a separation zone for separating the effluent exiting the reaction zone and recovering the different products obtained, a purification zone for purification of the olefin(s) produced.

As regards the pressure in step (b), the pressure of the reaction zone in the dehydration unit step (b) can be any pressure but it is more economical to operate at moderate pressure. By way of example the pressure of the reaction zone ranges from 0.5 to 30 bars absolute (50 kPa to 3 MPa), advantageously from 0.5 to 20 bars absolute (50 kPa to 2 MPa), advantageously from 1 to 20 bars absolute (0.1 MPa to 2 MPa), more advantageously from 1 to 17 bars absolute (0.1 MPa to 1.7 MPa). Advantageously, the partial pressure of the alcohols is advantageously lower than 10 bars absolute (1 MPa) and more advantageously from 0.1 to 4 bars absolute (0.01 MPa to 0.4 MPa), preferably lower than 3.5 bars absolute (0.35 MPa) and more preferably lower than 3 bars absolute (0.3 MPa).

As regards the temperature of the reaction zone in the dehydration unit, it ranges advantageously from 220° C. to 500° C., advantageously from 250° C. to 500° C., more advantageously from 280° C. to 500° C. and preferably from 300° C. to 450° C.

In a reaction zone operating in adiabatic mode, these temperatures refer substantially to the temperature of the alcohol feed entering into the reaction zone. For example, the feed enters at a temperature from 300° C. to 500° C. and exits the reactor at a temperature from 220 to 450° C.

In a reactor operating in isothermal mode, these temperatures refer substantially to the average catalyst bed temperature and can range from 220 to 450° C.

The ethanol dehydration is an endothermic reaction and requires the input of reaction heat in order to maintain catalyst activity sufficiently high and shift the thermodynamic equilibrium to sufficiently high conversion levels.

In case of fluidised bed reactors: (i) for stationary fluidised beds without catalyst circulation, the average catalyst bed temperature is substantially homogeneous throughout the catalyst bed; (ii) in case of circulating fluidised beds where catalyst circulates between a converting reaction section and a catalyst regeneration section, depending on the degree of catalyst backmixing the temperature in the catalyst bed approaches homogeneous conditions (a lot of backmixing) or approaches plug flow conditions (nearly no backmixing) and hence a decreasing temperature profile will install as the conversion proceeds.

In case of fixed bed or moving bed reactors, a decreasing temperature profile will install as the conversion of the alcohol proceeds. In order to compensate for temperature drop and consequently decreasing catalyst activity or approach to thermodynamic equilibrium, reaction heat can be introduced by using several catalyst beds in series with interheating of the reactor effluent from the first bed to higher temperatures and introducing the heated effluent in a second catalyst bed, etc. When fixed bed reactors are used, a multi-tubular reactor can be used where the catalyst is loaded in small-diameter tubes that are installed in a reactor shell. At the shell side, a heating medium is introduced that provides the required reaction heat by heat-transfer through the wall of the reactor tubes to the catalyst.

As regards the WHSV of the composition (A), it ranges advantageously from 0.1 to 30 h$^{-1}$, advantageously from 1 to 25 h$^{-1}$, more advantageously from 3 to 25 h$^{-1}$, more preferably from 4 to 25 h$^{-1}$.

As regards the effluent (B), it comprises essentially water, olefin(s), the inert component (if any) and unconverted alcohol(s). Said unconverted alcohol(s) is supposed to be as less as possible. The olefin(s) is (are) recovered by usual fractionation means. Advantageously the inert component, if any, is recycled in the feed (A)-providing step (a) as well as unconverted alcohol(s), if any. Optionally, a part of the water is recovered by fractionation and recycled to the dehydration unit in step (a).

As regards the dehydration catalyst of step (b), it can be any acid catalyst capable to cause the dehydration of alcohols under above said conditions. One can cite molecular sieves, zeolites, modified zeolites (including P-modified zeolites), silica-alumina, alumina, silicated, titanated, zirconated or fluorinated alumina, silico-aluminophosphates, as well as modified crystalline aluminosilicate of the Framework Type FER having Si/Al framework molar ratio greater than 20 and a ratio between strong acid sites and weak acid sites, S/W, lower than 1.0.

According to an embodiment the catalyst is a crystalline silicate containing advantageously at least one 10 members ring into the structure. It is by way of example of the MFI (ZSM-5, silicalite-1, boralite C, TS-1), MEL (ZSM-11, silicalite-2, boralite D, TS-2, SSZ-46), FER (Ferrierite, FU-9, ZSM-35), MTT (ZSM-23), MWW (MCM-22, PSH-3, ITQ-1, MCM-49), TON (ZSM-22, Theta-1, NU-10), EUO (ZSM-50, EU-1), MFS (ZSM-57) and ZSM-48 family of microporous materials consisting of silicon, aluminium, oxygen and optionally boron. Advantageously in said first embodiment the catalyst (A1) is a crystalline silicate or a dealuminated crystalline silicate.

The crystalline silicate can have a ratio Si/Al of at least about 10.

The crystalline silicate, in an embodiment, can have a ratio Si/Al of at least about 100 and is advantageously selected among the MFI and the MEL.

The crystalline silicate and the dealuminated crystalline silicate are essentially in H-form. It means that a minor part (less than about 50%) can carry metallic compensating ions e.g. Na, Mg, Ca, La, Ni, Ce, Zn, Co.

The dealuminated crystalline silicate is advantageously such as about 10% by weight of the aluminium is removed. Such dealumination is advantageously made by a steaming optionally followed by a leaching.

In another specific embodiment the crystalline silicate catalyst is mixed with a binder, preferably an inorganic binder, and shaped to a desired shape, e.g. pellets. The binder is selected so as to be resistant to the temperature and other conditions employed in the dehydration process of the invention. The binder is an inorganic material selected from clays, silica, metal silicate, metal oxides (such as $ZrO_2$) or gels including mixtures of silica and metal oxides.

According to an embodiment the catalyst is a P-modified zeolite (Phosphorus-modified zeolite). Said phosphorus modified molecular sieves can be prepared based on MFI, MOR, MEL, clinoptilolite or FER, MWW, TON, EUO, MFS and ZSM-48 family of microporous molecular sieves having an initial Si/Al ratio advantageously between 4 and 500. The P-modified zeolites of this recipe can be obtained based on cheap crystalline silicates with low Si/Al ratio (below 30).

By way of example said P-modified zeolite is made by a process comprising in that order:
selecting a zeolite (advantageously with Si/Al ratio between 4 and 500) among H$^+$ or NH$_4^+$-form of MFI, MEL, FER, MOR, clinoptilolite, MWW, TON, EUO, MFS and ZSM-48;
introducing P at conditions effective to introduce advantageously at least 0.05 wt % of P;
separation of the solid from the liquid if any;
an optional washing step or an optional drying step or an optional drying step followed by a washing step;
a calcination step;

The zeolite with low Si/Al ratio has been made previously with or without direct addition of an organic template.

Optionally the process to make said P-modified zeolite comprises the steps of steaming and leaching. The method consists in steaming followed by leaching. It is generally known by the persons in the art that steam treatment of zeolites, results in aluminium that leaves the zeolite framework and resides as aluminiumoxides in and outside the pores of the zeolite. This transformation is known as dealumination of zeolites and this term will be used throughout the text. The treatment of the steamed zeolite with an acid solution results in dissolution of the extra-framework aluminiumoxides. This transformation is known as leaching and this term will be used throughout the text. Then the zeolite is separated, advantageously by filtration, and optionally washed. A drying step can be envisaged between filtering and washing steps. The solution after the washing can be either separated, by way of example, by filtering from the solid or evaporated.

P can be introduced by any means or, by way of example, according to the recipe described in U.S. Pat. Nos. 3,911,041, 5,573,990, WO2009016153, WO 2011089262, WO2013017496, WO2013017497, WO2013017498, and U.S. Pat. No. 6,797,851.

The catalyst made of a P-modified zeolite can be the P-modified zeolite itself or it can be the P-modified zeolite formulated into a catalyst by combining with other materials that provide additional hardness or catalytic activity to the finished catalyst product. Advantageously, at least a part of phosphorous is introduced into zeolite before shaping. In a specific embodiment, the formed P-precursor can be further modified with the metals selected from Mg, Ca, La, Ni, Ce, Zn, Co, Ag, Fe, Cu according to the recipe described in WO 09092779 and WO 09092781.

The separation of the liquid from the solid is advantageously made by filtering at a temperature between 0-90° C., centrifugation at a temperature between 0-90° C., evaporation or equivalent.

Optionally, the zeolite can be dried after separation before washing. Advantageously said drying is made at a temperature between 40-600° C., advantageously for 1-10 h. This drying can be processed either in a static condition or in a gas flow. Air, nitrogen or any inert gases can be used.

The washing step can be performed either during the filtering (separation step) with a portion of cold (<40° C.) or hot water (>40 but <90° C.) or the solid can be subjected to a water solution (1 kg of solid/4 liters water solution) and treated under reflux conditions for 0.5-10 h followed by evaporation or filtering.

Final equilibration step is performed advantageously at the temperature 400-800° C. either in a static condition or in a gas flow. Air, nitrogen or any inert gases can be used.

According to a specific embodiment the phosphorous modified zeolite is made by a process comprising in that order:
- selecting a zeolite (advantageously with Si/Al ratio between 4 and 500, from 4 to 30 in a specific embodiment) among $H^+$ or $NH_4^+$-form of MFI, MEL, FER, MOR, clinoptilolite, MWW, TON, EUO, MFS and ZSM-48;
- steaming at a temperature ranging from 400 to 870° C. for 0.01-200 h;
- leaching with an aqueous acid solution at conditions effective to remove a substantial part of Al from the zeolite;
- introducing P with an aqueous solution containing the source of P at conditions effective to introduce advantageously at least 0.05 wt % of P;
- separation of the solid from the liquid;
- an optional washing step or an optional drying step or an optional drying step followed by a washing step;
- a calcination step.

Optionally between the steaming step and the leaching step there is an intermediate step such as, by way of example, contact with silica powder and drying.

Optionally the leaching and introducing P are made simultaneously by using an acid based comprising phosphorus to make the leaching.

Advantageously the selected MFI, MEL, FER, MOR, clinoptilolite, MWW, TON, EUO, MFS and ZSM-48 (or $H^+$ or $NH_4^+$-form MFI, MEL, FER, MOR, clinoptilolite, MWW, TON, EUO, MFS and ZSM-48) has an initial atomic ratio Si/Al of 100 or lower and from 4 to 30 in a specific embodiment. The conversion to the $H^+$ or $NH_4^+$-form is known per se and is described in U.S. Pat. Nos. 3,911,041 and 5,573,990.

Advantageously the final P-content is at least 0.05 wt % and preferably between 0.3 and 7 w %. Advantageously at least 10% of Al, in respect to parent zeolite MFI, MEL, FER, MOR and clinoptilolite, MWW, TON, EUO, MFS and ZSM-48, have been extracted and removed from the zeolite by the leaching.

Then the zeolite either is separated from the washing solution or is dried without separation from the washing solution. Said separation is advantageously made by filtration. Then the zeolite is calcined, by way of example, at 400° C. for 2-10 hours.

In the steam treatment step, the temperature is preferably from 420 to 870° C., more preferably from 480 to 760° C. The pressure is preferably atmospheric pressure and the water partial pressure may range from 13 to 100 kPa. The steam atmosphere preferably contains from 5 to 100 vol % steam with from 0 to 95 vol % of an inert gas, preferably nitrogen. The steam treatment is preferably carried out for a period of from 0.01 to 200 hours, advantageously from 0.05 to 200 hours, more preferably from 0.05 to 50 hours. The steam treatment tends to reduce the amount of tetrahedral aluminium in the crystalline silicate framework by forming alumina.

The leaching can be made with an organic acid such as citric acid, formic acid, oxalic acid, tartaric acid, malonic acid, succinic acid, glutaric acid, adipic acid, maleic acid, phthalic acid, isophthalic acid, fumaric acid, nitrilotriacetic acid, hydroxyethylenediaminetriacetic acid, ethylenediaminetetracetic acid, trichloroacetic acid trifluoroacetic acid or a salt of such an acid (e.g. the sodium salt) or a mixture of two or more of such acids or salts. The other inorganic acids may comprise an inorganic acid such as nitric acid, hydrochloric acid, methansulfuric acid, phosphoric acid, phosphonic acid, sulfuric acid or a salt of such an acid (e.g. the sodium or ammonium salts) or a mixture of two or more of such acids or salts.

The residual P-content is adjusted by P-concentration in the aqueous acid solution containing the source of P, drying conditions and a washing procedure if any. A drying step can be envisaged between filtering and washing steps.

Said P-modified zeolite can be used as itself as a catalyst. In another embodiment it can be formulated into a catalyst by combining with other materials that provide additional hardness or catalytic activity to the finished catalyst product. Materials which can be blended with the P-modified zeolite can be various inert or catalytically active materials, or various binder materials. These materials include compositions such as kaolin and other clays, various forms of rare earth metals, phosphates, alumina or alumina sol, titania, zirconia, quartz, silica or silica sol, and mixtures thereof. These components are effective in densifying the catalyst and increasing the strength of the formulated catalyst. The catalyst may be formulated into pellets, spheres, extruded into other shapes, or formed into a spray-dried particles. The amount of P-modified zeolite which is contained in the final catalyst product ranges from 10 to 90 weight percent of the total catalyst, preferably 20 to 70 weight percent of the total catalyst.

A dehydration catalyst has already been described in WO2009098262.

According to an embodiment the catalyst is a modified crystalline aluminosilicate of the Framework Type FER having Si/Al framework molar ratio greater than 20 and a ratio between strong acid sites and weak acid sites, S/W, lower than 1.0. The ratio S/W is measured by temperature-programmed desorption of ammonia and is determined by the ratio of the peak area of desorbed ammonia above 340° C. to the peak area of desorbed ammonia below 340° C.

In a preferred embodiment, the Framework Type FER is a crystalline aluminosilicate containing advantageously at least one 10 members ring into the structure based on T-atoms, i.e. on the Al and Si atoms contained in said ring. The family of Framework Type FER includes Ferrierite.

In a preferred embodiment, the modified crystalline aluminosilicate of the Framework Type FER is selected from Ferrierite, FU-9, Nu-23, ISI-6, ZSM-35 and SUZ-4. Preferably, the modified crystalline aluminosilicate of the Framework Type FER is Ferrierite.

As mentioned above, the Si/Al framework molar ratio of the modified crystalline aluminosilicate may be greater than 20, preferably, the Si/Al framework molar ratio of the modified crystalline aluminosilicate may be at most 150. Advantageously the modified crystalline aluminosilicate shows a high crystallinity of its zeolite phase, said crystallinity being similar to the crystallinity of the parent zeolite before modification. A similar crystallinity is evidenced via the X ray diffraction patterns (less than 20% of difference measured on the area below the X ray curves).

In a preferred embodiment, the ratio of strong acid sites to weak acid sites, S/W, in said modified crystalline aluminosilicate may be greater than 0.1.

In a preferred embodiment, said modified crystalline aluminosilicate has content in redox metals or cations thereof lower than 1000 ppm, said metals belonging to one of columns 3 to 12 of the Periodic Table. Preferably, said metals are Fe, Co, Ni, Cu, Mo, Mn, Ti, Zn, V, Cr, Ru, Rh, Cd, Pt, Pd, Au, Zr.

In another specific embodiment, the catalyst is mixed with a binder, preferably an inorganic binder. The binder is selected so as to be resistant to the temperature and other conditions employed in the dehydration process of the invention. The binder is an inorganic material selected from clays, silica, metal silicate, metal oxides (such as $ZrO_2$), alumina, aluminophosphate binders, in particular, stoichiometric amorphous aluminophosphate or gels including mixtures of silica and metal oxides.

The modified crystalline aluminosilicate may be in H-form. The H-form of a modified crystalline aluminosilicate of the Framework Type FER means that it comprises oxygen atoms bonded to one aluminium atom and one silicon atom, and which is protonated with a hydrogen atom, resulting in the following sequence —[—Al—O(H)—Si—]—. In the present invention, the modified crystalline aluminosilicate may be essentially under H-form, which means containing less than 1000 ppm of the total amount of the alkali ions and the alkaline earth ions. In another embodiment, the modified crystalline aluminosilicate is partly under H-form. It means that in said modified crystalline aluminosilicate part of the hydrogen atoms bonded to oxygen atoms in the following sequence —[—Al—O(H)—Si—]— is substituted by metallic ions, preferably alkali ions, alkaline earth ions or silver ions. In a preferred embodiment, the modified crystalline aluminosilicate comprises the sequences —[—Al—O(H)—Si—]— and —[—Al—O(X)—Si—]— wherein X is alkali ions, alkaline earth ions or silver ions, the sequence —[—Al—O(X)—Si—]— representing less than 75% based on the total amount of sequences —[—Al—O(H)—Si—]— and —[—Al—O(X)—Si—]— in said modified crystalline aluminosilicate, preferably the sequence —[—Al—O(X)—Si—]— represents less than 50%. Preferably, the alkali ions or alkaline earth ions may be Na, K, Cs, Li, Mg or Ca.

Alternatively, the modified crystalline aluminosilicate may have content in one of the elements selected from the group consisting of lithium, sodium, cesium, magnesium, calcium, potassium and silver, independently from one another, ranging from 10 to 10000 ppm.

According to a specific embodiment the modified crystalline aluminosilicate of the Framework Type FER is made by a process comprising the steps of:
1) providing a crystalline aluminosilicate of the Framework Type FER having Si/Al framework molar ratio greater than or equal to 20, and
2) treating said crystalline aluminosilicate to form a modified crystalline aluminosilicate of the Framework Type FER wherein the Si/Al framework molar ratio is greater than 20 (from 20 to 150 in a specific embodiment), and wherein the ratio of strong acid sites to weak acid sites S/W is lower than 1.0 (greater than 0.1 in a specific embodiment),
3) optionally drying said modified crystalline aluminosilicate formed in step (B) at temperature ranging from 50° C. to 200° C. for a period ranging from 30 min to 24 h, preferably from 1 h to 15 h,
4) optionally, subsequently to the drying step (C), calcining said modified crystalline aluminosilicate formed in step (B) at temperature ranging from 200° C. to 920° C. for a period ranging from 1 h to 48 h.

In a preferred embodiment, the crystalline aluminosilicate of the group Framework Type FER provided in step (1) is selected from Ferrierite, FU-9, Nu-23, ISI-6, ZSM-35 and SUZ-4. Preferably, the crystalline aluminosilicate of the Framework Type FER is Ferrierite. Preferably, the crystalline aluminosilicate provided in step (1) has a ratio of strong acid sites to weak acid sites greater than or equal to 1.0

Preferably, the treatment of step (2) allowing the formation of the modified crystalline aluminosilicate of the Framework Type FER may comprise one or more of the following steps:
(i) treating said crystalline aluminosilicate of the Framework Type FER with an acidic medium, or
(ii) applying partial ion exchange to said crystalline aluminosilicate of the Framework Type FER, or
(iii) selectively poisoning strong acid sites of the crystalline aluminosilicate of the Framework Type FER by adding a solution comprising alkali salts or alkaline earth salts.

Any of the treatment steps (i) to (iii) may be repeated until the modified crystalline aluminosilicate so-formed reaches the required values with respect to the Si/Al framework molar ratio and with respect to the ratio of strong to weak acid sites. Two or more of the treatment steps (i) to (iii) may be combined together to form the modified crystalline aluminosilicate as defined herein. For example, step (i) or (iii) may be subsequently combined with step (ii) to enhance the properties of the modified crystalline aluminosilicate, in particular of the modified crystalline ferrierite, and of the catalyst composition comprising the same in terms of selectivity, activity or regenerability.

Step (i) of treatment of said crystalline aluminosilicate of the Framework Type FER in an acidic medium may comprise the step of contacting said crystalline aluminosilicate of the Framework Type FER, provided in step (1), with a solution, preferably an aqueous solution, containing one or more organic compounds, each organic compound comprising one or more —$CO_2H$, —$SO_3H$ or —$SO_4H$ groups or salts thereof, preferably two or more —$CO_2H$, —$SO_3H$ or —$SO_4H$ groups or salts thereof. These organic compounds may for example be selected from the group consisting of citric acid, maleic acid, ethylenediaminetetracetic acid, tartaric acid, fumaric acid, oxalic acid, malonic acid, succinic acid, adipic acid, glutaric acid or itaconic acid, phtalic acid, isophtalic acid, nitrilotriacetic acid, hydroxyethylenediaminetriacetic acid, or salts thereof or mixture thereof. The concentration in each one or more organic compounds in said solution may range from $1 \cdot 10^{-4}$M to 10M, preferably from $1 \cdot 10^{-3}$M to 1M. Step (i) may be carried out at temperature ranging from 10° C. to 110° C., preferably from 20° C. to 80° C., preferably from 30 min to 24 h, more preferably from 1 h to 12 h.

Preferably, in said solution, said one or more organic compounds may be under the form of water soluble salt, preferably sodium, potassium, magnesium, calcium, lithium, cesium or silver salt or mixture thereof. When a salt of said one or more organic compounds is used, the amount and the concentration of the solution comprising the same can be adjusted such that, in the so-formed modified crystalline aluminosilicate, the sequence —[—Al—O(X)—Si—]— wherein X is alkali, alkaline earth or silver ions, represents at most 75% of the total amount of sequences —[—Al—O(X)—Si—]— and —[—Al—O(X)—Si—]—, preferably at most 50%, more preferably at most 25%, and preferably at least 1%, more preferably at least 5%, most preferably at least 10%.

The step (ii) of applying ion exchange to the crystalline aluminosilicate to form the modified crystalline aluminosilicate may be carried out by contacting said crystalline aluminosilicate with a solution containing one or more inorganic salts such as inorganic ammonium salt, inorganic calcium salt, inorganic lithium salt, inorganic sodium salt, inorganic potassium salt, inorganic magnesium salt or inorganic silver salt. Inorganic salt may be salt of nitric acid, halogenic acid, sulfuric acid, sulfurous acid, nitrous acid or mixture thereof, preferably nitric acid or halogenic acid or mixture thereof. The concentration of each inorganic salt in said solution may range from $1 \cdot 10^{-4}$M to 10M, preferably from $1 \cdot 10^{-3}$M to 1M. Step (ii) may be carried out at temperature ranging from 10° C. to 110° C., preferably from 20° C. to 80° C., preferably for 30 min to 24 h, more preferably for 1 h to 10 h. Preferably, the solution may contain ammonium salt, calcium salt or lithium salt of nitric acid or halogenic acid.

The step (iii) of selectively poisoning strong acid sites of the crystalline aluminosilicate to form the modified crystalline aluminosilicate may be carried out by impregnating said crystalline aluminosilicate of step (1) with an aqueous solution containing alkali ions or alkaline earth ions, preferably sodium, lithium, potassium, cesium, magnesium or calcium ions or mixture thereof. The amount and the concentration of said aqueous solution containing alkali ions or alkaline earth ions can be adjusted such that in the so-formed modified crystalline aluminosilicate, the sequence —[—Al—O(X)—Si—]— wherein X is alkali ions or alkaline earth ions, as defined above, represents at most 75% of the total amount of sequences —[—Al—O(X)—Si—]— and —[—Al—O(X)—Si—]—, preferably at most 50%, more preferably at most 25%, and preferably at least 1%, more preferably at least 5%, most preferably at least 10%. In particular, the concentration of said solution ranges from $1 \cdot 10^{-4}$M to 10M, preferably from $1 \cdot 10^{-3}$M to 5M. Step (iii) may be carried out at temperature ranging from 10° C. to 100° C., preferably from 20° C. to 30° C. The suspension or solution formed by contacting said crystalline aluminosilicate of step (1) with an aqueous solution containing alkali ions or alkaline earth ions may be further heated at temperature ranging from 50° C. to 100° C., for a period ranging from 1 h to 24 h.

Prior or subsequently to step (2) of the present process, the modified crystalline aluminosilicate or the crystalline aluminosilicate may be mixed with a binder, preferably an inorganic binder. Typically, the binder and the crystalline aluminosilicate, modified or not, are mixed together by a mixing process. In such a process, the binder, for example silica, in the form of a gel is mixed with the crystalline aluminosilicate, modified or not. The resultant mixture is extruded into the desired shape, for example cylindrical or multi-lobe bars. Spherical shapes can be made in rotating granulators or by oil-drop technique. Small spheres can further be made by spray-drying a catalyst-binder suspension. Thereafter, the extruded material containing the binder and the crystalline aluminosilicate, modified or not, is calcined in air or an inert gas, typically at a temperature of from 200 to 900° C. for a period of from 1 to 48 hours. Preferably, said binder is selected from the group consisting of clays, alumina, silica-alumina, silica, titania, aluminophosphate, titania-silica. Hence, according to the present process, the crystalline aluminosilicate provided in step (1) may encompass the extruded material containing the binder and the crystalline aluminosilicate as described herein.

According to another specific embodiment, suitable catalysts for the present process are silicoaluminophosphate molecular sieves, in particular of the AEL group with typical example the SAPO-11 molecular sieve. The SAPO-11 molecular sieve is based on the ALPO-11, having essentially an Al/P ratio of 1 atom/atom. During the synthesis silicon precursor is added and insertion of silicon in the ALPO framework results in an acid site at the surface of the micropores of the 10-membered ring sieve. The silicon content ranges from 0.1 to 10 atom % (Al+P+Si is 100).

According to another specific embodiment, another family of suitable catalysts for the dehydration are alumina's as such, silica-alumina's or alumina's that have been modified by surface treatment with silicon, zirconium, titanium or fluor. Alumina's are generally characterized by a rather broad acid strength distribution and having both Lewis-type and Bronsted-type acid sites. The presence of a broad acid strength distribution makes the catalysis of several reactions, requiring each a different acid strength, possible. This often results in low selectivity for the desired product. Deposition of silicon, zirconium, titanium or fluor on the surface of alumina allows rendering the catalyst significantly more selective. For the preparation of the alumina based catalyst, suitable commercial alumina's can be used, preferably eta or gamma alumina, having a surface area of 10 to 500 m$^2$/gram and an alkali content of less than 0.5%. The catalyst according to the present invention is prepared by adding 0.05 to 10% of silicon, zirconium or titanium. The addition of these metals can be done during the preparation of the alumina or can be added to the existing alumina, eventually already activated. Addition of the metal during the preparation of the alumina can be done by dissolving the metal precursor together with the aluminium precursor before precipitation of the final alumina or by addition of the metal precursor to the aluminium hydroxide gel. A preferred method is adding metal precursors to the shaped alumina. Metal precursors are dissolved in a suitable solvent, either aqueous or organic, and contacted with the alumina by incipient wetness impregnation or by wet impregnation or by contacting with an excess of solute during a given time, followed by removing the excess solute. The alumina can also be contacted with vapour of the metal precursor. Suitable metal precursors are halides of silicon, zirconium or titanium, oxyhalides of zirconium or titanium; alcoxides of silicon, zirconium or titanium; oxalates or citrates of zirconium or titanium or mixtures of the above. The solvent is selected according to the solubility of the metal precursor. The contacting can be done at temperature of 0° C. to 500° C., most preferred from 10° C. to 200° C. After the contacting, the alumina is eventually washed, dried and finally calcined in other to enhance the surface reaction between the silicon, zirconium or titanium and the alumina and the removal of the metal precursor ligands. The use of silicated, zirconated or titanated or fluorinated alumina's for the dehydration is preferably done in the presence of water. The weight ratio of water to alcohol ranges from 1/25 to 3/1. Fluorinated alumina is known in itself and can be made according to the prior art.

According to an embodiment the catalyst is any of above cited catalyst which is subjected to a preliminary in-situ or ex-situ pre-coking step before use. The pre-coking step may be performed in presence of the alcohol to dehydrate, preferably in presence of iso-butanol. In a first embodiment, the pre-coking may be performed at a temperature from 300° C. to 450° C., advantageously from 400° C. to 450° C., under a pressure from 0.1 to 0.5 MPa and a WHSV from 0.1 to 3 $h^{-1}$. In another embodiment, the pre-coking step may be performed at a temperature from 250 to 450° C., preferably from 300 to 350° C., a pressure from 1.1 to 3 MPa, preferably from 1.2 and 3 MPa and a WHSV from 0.1 and 3 $h^{-1}$. In both embodiments, pre-coking may be performed during 2 to 30 hours, preferably from 6 to 24 hours. Advantageously, the precooking is either performed at a temperature higher than the dehydration temperature or at a pressure higher than the dehydration pressure.

As regards the addition of compound(s) with acidic character capable to reduce the undesired by-products, one or more compound chosen among organic acids is added to feed (A) or directly in the dehydration unit such that the undesired by-products in the effluent (B) are reduced by comparison with a non introduction of said organic compound.

The man skilled in the art can easily determine, by following the by-products in the effluent and the percentage of said by-products whether an organic acid is appropriate. Undesired by-products are aldehyde(s), in particular aldehyde(s) corresponding to the alcohol(s) to dehydrate, as well as $H_2$, CO and $CH_4$.

Significant improvement can be achieved in case of introduction of advantageously at least 0.1 wt % of organic acid relative to the alcohol.

The term "organic acid" refers to the definition generally accepted i.e. organic molecules having acidic properties. However, in the context of the invention, the term "organic acid" does not refer to organic compound having heteroelements such as alkali metals (except hydrogen), alkaline earth metals, transition metals, or halogens or elements such as phosphor, sulphur or nitrogen.

Organic acid(s) may advantageously be chosen among carboxylic acid(s), in particular containing one, two or three carboxyl functional groups C(O)OH. Said carboxylic acid may eventually be an alpha hydroxyl acid.

Advantageously, carboxylic acid(s) may contain from 1 to 10 carbon atoms.

Preferably, said carboxylic acid has the same number of carbon atoms or less than the alcohol to dehydrate. Most preferably, carboxylic acid(s) is (are) the acid(s) corresponding to the alcohol(s) to dehydrate, in other words the carboxylic acid(s) having a same number of carbon atoms than the alcohol.

Carboxylic acid may for example be chosen among formic acid, acetic acid, propanoic acid, iso-propanoic acid, butanoic acid, iso-butanoic acid, pentanoic acid, oxalic acid, succinic acid, glutaric acid, adipic acid, maleic acid, fumaric acid, tartaric acid, malonic acid, citric acid.

Amounts of organic acid(s) can range from 0.1 to 100 wppm, advantageously from 0.1 to 50 wppm, preferably from 0.1 to 25 wppm, more preferably from 0.1 to 10 wppm, relative to the alcohol.

The organic acid(s) can be introduced in the dehydration unit by (i) blending with the alcohol feedstock, (ii) blending with a part of the alcohol feedstock which is subsequently introduced in the dehydration unit with the remaining alcohol feedstock, (iii) blended with the inert diluent which is subsequently introduced in the dehydration unit with the alcohol feedstock, (iv) blended with water which is subsequently introduced in the dehydration unit with the alcohol feedstock or (v) blended with one of the streams that is recycled back to the dehydration unit, like non-converted alcohol, water or inert diluents.

Eventually, organic acid(s) may be only contained in a stream recycled back to the dehydration unit, like non converted alcohol, water or inert diluents, without the need to add further organic acid from an external source.

Organic acid-(s) may also be introduced by (vi) blending an alcohol feedstock being substantially free from organic acid(s) with an alcohol feedstock containing already in the range of 0.1 wppm to 100 wppm of organic acid. In the latter case the organic acid is originating from the production process where the alcohol feedstock was produced as for instance the fermentation process of carbohydrates or synthesis gas into alcohol where trace amounts of organic acids are inherently part of the production process and are left in the final alcohol product. In an embodiment, only alcohol feedstock already containing organic acid(s) in appropriate quantities is used.

EXAMPLES

The ethanol conversion is the ratio (ethanol introduced in the reactor-ethanol leaving the reactor)/(ethanol introduced in the reactor).

The ethylene yield is the ratio, on carbon basis, (ethylene leaving the reactor)/(ethanol introduced in the reactor).

The ethylene selectivity is the ratio, on carbon basis, (ethylene leaving the reactor)/(ethanol converted in the reactor).

The C2's cut purity is the ratio, on carbon basis, (ethylene leaving the reactor)/(ethylene+ethane leaving the reactor). It means the ethylene purity is the percentage of ethylene, on a carbon basis, present in the $C_2$ cut, containing close-boiling compounds, recovered in the stream leaving the reactor. The $C_2$ cut comprises ethylene and ethane but doesn't comprise the unconverted ethanol and acetaldehyde if any.

Experimental

Tests were performed on 2.5 g of catalyst grains (35-45 meshes) blended homogeneously with SiC to obtain 10 ml of volume. The catalyst/SiC blend was loaded in a tubular reactor with internal diameter 11 mm.

The temperature profile is monitored with the aid of a thermowell placed inside the reactors. The reactor temperature is increased at a rate of 60° C./h to 550° C. under nitrogen, kept 1 hour at 550° C. and then cooled down to the initial reaction temperature under nitrogen. The nitrogen is then replaced by the feed at the indicated operating conditions.

Analysis of the products is performed by using on-line chromatography:
- a gas chromatography with a FID (flame ionization detector), for measuring ethylene, acetaldehyde and other hydrocarbons in totality of the effluent,
- a gas chromatography with a TCD (thermal conductivity detector) for measuring CO, $CO_2$, $H_2$ and $CH_4$ The total amount of the acids in the feed containing alcohol or in the liquid part of the effluent is measured by Ion chromatography. The Dionex ICS-2000 Ion Chromatography system (ISC-2000) with suppressed conductivity detection is used. Before running the system, the ion-chromatography system was calibrated using a standard solution of ethanol.

Raw Bio-Ethanol (Ethanol Surfin)

The characteristics of the raw bio-ethanol used in the example below are gathered table 1.

TABLE 1

Main characteristics of Surfin bio-ethanol

|  |  | Ethanol Surfin (food industry) |
|---|---|---|
| Density @ 15° C. | g/ml | 0.8100 |
| EtOH content | wt % | 94.5 |
| Sulfur | ppm | <0.5 |
| Other impurities |  |  |
| Aldehydes | ppm | 7 |
| Esters | ppm | 0 |
| Higher alcohol | ppm | 10 |
| Acids | ppm | <1 |

Catalyst:

The catalyst is a phosphorous modified zeolite (P-ZSM5), prepared according to the following recipe. A sample of zeolite ZSM-5 (Si/Al=12) in NH4-form (containing 250 ppm of Na & synthesized without template) was blended with a silica binder in a weight ratio 80:20 followed by addition of extrusion additives and shaping. A final Na content in the catalyst was 320 wppm. The extruded sample was dried for 2 h at 140° C., calcined for 2 h at 600° C. followed by steaming at 550° C. for 6 h in 100% steam.

Steamed solid was incipient wetness impregnated with an aqueous solution of phosphoric acid to introduce about 3 wt % of phosphorus to the catalyst. The impregnated solid was dried for 16 h at 110° C.

Then, the phosphated sample was incipient wetness impregnated with a solution of calcium nitrate obtained by dissolution of calcium carbonate to introduce about 1 wt % of calcium to the solid. The impregnated solid was dried for 16 h at 110° C. Resulted catalyst containing 2.8 wt % of phosphorus and 0.8% of calcium was steamed at 750° C. for 1 h in 100% steam.

Example

A pure EtOH (surfin, 94.5 wt % alcohol-water) was subjected to a contact with catalyst in a fixed bed reactor at 390° C., WHSV=21 $h^{-1}$, P=2 bara followed by a switching to a EthOH surfin feed doped with 0.87 wt % of Acetic acid. Afterwards, the feed was changed back to the EtOH surfin (94.5 wt % alcohols) to make a return point.

The results are given in table 2 hereunder. The values are given in weight percents on carbon basis, coke free basis.

TABLE 2

Results of Dehydration of EtOH with and without Acetic acid addition

| FEED | Surfin 100% | Surfin + 0.87% AcAc | | Surfin 100% |
|---|---|---|---|---|
| T(° C.) | 390 | 390 | 390 | 390 |
| Conversion (% wt CH2) | 99.86 | 99.9 | 99.3 | 99.1 |
| Acetaldehyde | 0.49 | 0.23 | 0.23 | 0.89 |
| DEE | 0.03 | 0.01 | 0.01 | 0.01 |
| EtOH | 0.14 | 0.15 | 0.65 | 0.92 |
| C2 | 0.19 | 0.14 | 0.14 | 0.18 |
| C2= | 97.10 | 98.00 | 97.56 | 96.42 |
| C3= | 0.33 | 0.11 | 0.10 | 0.15 |
| C4+ olef | 1.08 | 0.96 | 0.95 | 0.99 |
| Heavies | 1.72 | 1.35 | 1.30 | 1.43 |
| Selectivity C2= (%) | 97.24 | 98.14 | 98.20 | 97.32 |
| C2's purity (%) | 99.80 | 99.85 | 99.85 | 99.82 |
| TOS (h) | 4 | 75 | 125 | 168 |
| TOS (h) | 60 | 123 | 166 | 210 |
| Duration | 56 | 49 | 41 | 42 |
| H2 (ppm) | 2688 | 311 | 356 |  |
| CH4 (vppm) | 77 | 32 | 41 |  |
| CO (vppm) | 23 | 10 | 8 |  |
| CO2 (vppm) | 6 | 76 | 73 |  |

Data in the above table 2 show formation of a very high amount of the light products ($H_2$, $CH_4$, CO) and acetaldehyde during the first 56 hours of the test.

Formation of these light products, as well as production of aldehydes, is considerably reduced when acetic acid is added to the feed. Increased selectivity to ethylene and purity of C2's cut are also obtained, as well as ethylene yields.

If addition of acetic acid is stopped, formation of aldehydes increases once again to even higher level than at the beginning of the test whereas ethylene yield decreases to a level lower than at the beginning of the test.

The invention claimed is:

1. A process for dehydrating an alcohol to prepare corresponding one or more olefins, comprising:
   (a) providing a feed (A) comprising one or more alcohols having at least 2 carbon atoms and an organic acid in the amount of at least 0.05 wt % with respect to the total content of the feed, optionally water, optionally an inert component, in a dehydration unit,
   (b) placing the feed (A) into contact with an acidic catalyst in a reaction zone of the dehydration unit at conditions effective to dehydrate at least a portion of the alcohol to make an olefin or a mixture of olefins having the same number of carbon atoms as the alcohol,
   (c) recovering from the dehydration unit an effluent (B) comprising:
   an olefin or a mixture of olefins,
   water,
   undesired by-products including aldehydes and light products, comprising $H_2$, CO, $CH_4$,
   optionally the one or more unconverted alcohols if any,
   optionally the inert component,
   and wherein the acidic catalyst is at least one compound selected from the group consisting of:

a crystalline silicate zeolite having a ratio Si/Al higher than 10, a dealuminated crystalline silicate zeolite, a phosphorous modified zeolite, a silica-alumina, alumina, silicated, titanated, zirconated or fluorinated alumina, one or more silico-aluminophosphates, a modified crystalline aluminosilicate of the Framework Type FER having Si/Al framework molar ratio greater than 20 and a ratio between strong acid sites and weak acid sites, S/W, lower than 1.0, the ratio S/W being measured by temperature-programmed desorption of ammonia and being determined by the ratio of the peak area of ammonia desorbed above 340° C. to that desorbed below 340° C., or any of above cited acidic catalyst, which was subjected to a preliminary pre-coking step.

2. The process according to claim 1 wherein the dehydration unit comprises at least one metallic internal wall.

3. The process according to claim 1, wherein the organic acid is at least one compound selected from the group consisting of carboxylic acids.

4. The process according to claim 1, wherein:
the recovery step (c) comprises recovering the one or more unconverted alcohols, the process further comprising, subsequent to recovery step (c), a step of:
(d) recycling the unconverted alcohol to the feed (A)-providing step (a), in the dehydration unit.

5. The process according to claim 1, wherein the recovering step (c) comprises recovering the one or more olefin and the one or more unconverted alcohols, as well as each compound contained in the effluent (B), by means of fractionating.

6. The process according to claim 1, wherein the one or more alcohols provided in step (a) are bio-alcohol(s) issued from edible or non-edible biomass.

7. The process according to claim 1, wherein the one or more alcohols provided in step (a) are obtained via syn-gas route or synthesized via partial oxidation of paraffin.

8. The process according to claim 1, wherein the one or more alcohols provided in step (a) are produced via hydrogenation of corresponding aldehydes, ketones or acids issued from the edible or non-edible biomass.

9. The process according to claim 1, where the one or more olefins recovered in step c) are used for production of polymers and elastomers.

10. The process according to claim 1, where the one or more olefins recovered in step c) are used for production of fuel.

11. The process according to claim 1 wherein the dehydration unit is operated at a pressure ranging from 0.5 to 30 bars absolute (50 kPa to 3 MPa); and/or with a partial pressure of the one or more alcohols being lower than 10 bars absolute (1 MPa).

12. The process according to claim 1 where the dehydration unit is operated at a temperature ranging from 220° C. to 500° C.

13. The process according to claim 1, wherein the acidic catalyst is at least one compound selected from the group consisting of:

a crystalline silicate zeolite having a ratio Si/Al higher than 10, a dealuminated crystalline silicate zeolite, a phosphorous modified zeolite, a silica-alumina, silicated, titanated, zirconated or fluorinated alumina, one or more silico-aluminophosphates, a modified crystalline aluminosilicate of the Framework Type FER having Si/Al framework molar ratio greater than 20 and a ratio between strong acid sites and weak acid sites, S/W, lower than 1.0, the ratio S/W being measured by temperature-programmed desorption of ammonia and being determined by the ratio of the peak area of ammonia desorbed above 340° C. to that desorbed below 340° C., or any of above cited acidic catalyst, which was subjected to a preliminary pre-coking step.

\* \* \* \* \*